United States Patent [19]

Loeliger

[11] 4,193,931

[45] Mar. 18, 1980

[54] POLYENE COMPOUNDS

[75] Inventor: Peter Loeliger, Kaiseraugst, Switzerland

[73] Assignee: Hoffmann-La Roche Inc., Nutley, N.J.

[21] Appl. No.: 899,427

[22] Filed: Apr. 24, 1978

[30] Foreign Application Priority Data

May 4, 1977 [LU] Luxembourg ............................ 77254

[51] Int. Cl.² ................................................ C11C 3/02
[52] U.S. Cl. .............................. 424/308; 260/410.9 R; 260/408; 260/413; 260/448.2 B; 260/558 R; 260/592; 260/599; 260/606.5 F; 260/590 FA; 424/317; 424/318; 424/339; 424/343; 424/341; 424/311; 424/324; 568/633; 568/808; 568/659; 568/661; 560/56; 560/255; 562/466
[58] Field of Search ..................... 260/410.9 R, 558 R, 260/590, 408, 599, 588 R; 560/8, 56; 568/632, 808

[56] References Cited

U.S. PATENT DOCUMENTS

| 3,781,314 | 12/1973 | Bollag et al. ................ 260/410.9 |
| 3,931,257 | 1/1976 | Pawson ............................ 260/408 |
| 3,957,836 | 5/1976 | Morimoto et al. .............. 560/56 |
| 3,984,440 | 10/1976 | Bollag et al. .................. 260/408 |
| 4,054,589 | 10/1977 | Bollag et al. .................. 260/408 |

FOREIGN PATENT DOCUMENTS 2542600 4/1976 Fed. Rep. of Germany ........ 260/410.9

Primary Examiner—Paul J. Killos
Attorney, Agent, or Firm—Jon S. Saxe; Bernard S. Leon; George W. Johnston

[57] ABSTRACT

Novel 7-(substituted indanyl or naphthyl)-3-methyl-octa-2,4,6-triene derivatives useful as anti-tumor agents are disclosed.

21 Claims, No Drawings

POLYENE COMPOUNDS

SUMMARY OF THE INVENTION

This invention is directed to novel polyene compounds of the formula:

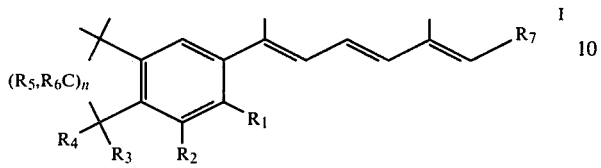

wherein $R_1$ and $R_2$ each are hydrogen, halogen or lower alkoxy; $R_3$, $R_4$, $R_5$ and $R_6$ each are hydrogen or lower alkyl; $R_7$ is hydroxymethyl, lower alkoxymethyl, lower alkanoyloxymethyl, carboxyl, lower alkoxycarbonyl, mono(lower alkyl)carbamoyl or di(lower alkyl)carbamoyl; and n is 1 or 2.

These polyene compounds are useful as anti-tumor agents as well as for the treatment of acne, psoriasis and other related dermatological disorders.

The compounds of formula I are produced via novel intermediate compounds which also come within the present invention.

DETAILED DESCRIPTION OF THE INVENTION

The present invention is concerned with polyene compounds of the formula:

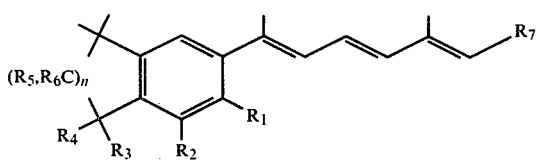

wherein $R_1$ and $R_2$ each are hydrogen, halogen or lower alkoxy; $R_3$, $R_4$, $R_5$ and $R_6$ each are hydrogen or lower alkyl; $R_7$ is hydroxymethyl, lower alkoxymethyl, lower alkanoyloxymethyl, carboxyl, lower alkoxycarbonyl, mono(lower alkyl)carbamoyl or di(lower alkyl)carbamoyl; and n is 1 or 2.

As used herein, "alkyl" refers to a monovalent substituent consisting solely of carbon and hydrogen of 1 to 20 carbon atoms which may be straight or branched chain. Lower alkyl denote straight and branched chain alkyl groups having 1 to 6 carbon atoms (e.g. methyl, ethyl, isopropyl and 2-methylpropyl).

Alkoxy refers to a monovalent substituent which consists of an alkyl group linked through an ether oxygen having its free valence bond from the ether oxygen. Lower alkoxy signifies straight or branched alkoxy groups having from 1 to 6 carbon atoms (e.g. methoxy, ethoxy and isopropoxy).

Lower alkanoyloxy refers to the residue of a lower alkylcarboxylic acid having 2 to 6 carbon atoms (e.g. acetic acid, propionic acid and pivalic acid) formed by removal of the hydrogen from the hydroxyl portion of the carboxyl group. Examples of lower alkanoyloxy groups are acetoxy, propionyloxy and hexanoyloxy.

Examples of mono(lower alkyl)carbamoyl and di(lower alkyl)carbamoyl groups are methylcarbamoyl, ethylcarbamoyl and diethylcarbamoyl.

Halogen denotes all four halogens, i.e. fluorine, chlorine, bromine and iodine.

Alkali metal includes any alkali metal such as lithium, sodium, potassium and caesium.

Alkaline earth metals include any of the conventional alkaline earth metals such as beryllium, magnesium, calcium and strontium.

The grouping "$R_5$, $R_6C$" denotes

wherein $R_5$ and $R_6$ are as above.

Preferred polyene compounds of formula I comprise those in which $R_3$, $R_4$, $R_5$ and $R_6$ each are hydrogen. Polyene compounds of formula I in which $R_1$ and $R_2$ each are hydrogen or lower alkoxy are also preferred. $R_7$ advantageously is lower alkoxycarbonyl, mono(lower alkyl)carbamoyl or di(lower alkyl)carbamoyl.

Examples of polyene compounds of formula I are:

all-trans-7-(1,1,3,3-tetramethyl-5-indanyl)-3-methyl-octa-2,4,6-trien-1-oic acid and the ethyl ester and ethylamide thereof, all-trans-7-(6-methoxy-1,1,3,3-tetramethyl-5-indanyl)-3-methyl-octa-2,4,6-trien-1-oic acid and the ethyl ester thereof, all trans-7-(3,3-dimethyl-5-indanyl)-3-methyl-octa-2,4,6-trien-1-oic acid and the ethyl ester thereof, all-trans-7-(7-methoxy-3,3-dimethyl-5-indanyl)-3-methyl-octa-2,4,6-trien-1-oic acid and the ethyl ester thereof, all-trans-7-(5,6,7,8-tetrahydro-5,5,8,8-tetramethyl-2-naphthyl)-3-methyl-octa-2,4,6-trien-1-oic acid and the ethyl ester thereof, and all-trans-7-(3-methoxy-5,6,7,8-tetrahydro-5,5,8,8-tetramethyl-2-naphthyl)-3-methyl-octa-2,4,6-trien-1-oic acid and the ethyl ester thereof.

According to the present invention, the polyene compounds of formula I are preferably produced by the following procedures:

Embodiment I: converting a ketone of the formula:

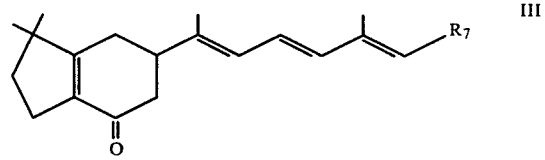

wherein $R_7$ is as above in a known manner into a compound of the formula:

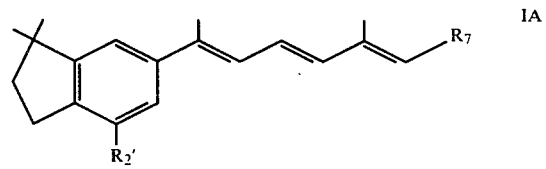

wherein $R'_2$ is hydrogen or lower alkoxy; and $R_7$ is as above; or

Embodiment II: reacting a compound of the formula:

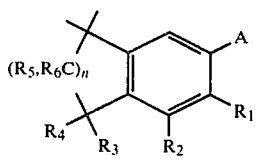

with a compound of the formula:

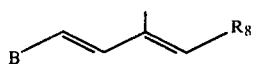

wherein $R_1$, $R_2$, $R_3$, $R_4$, $R_5$, $R_6$ and n are as above; A is 1-(triarylphosphonium)-ethyl of the formula $H_3C-CH-P[X]_3^{\oplus}Y^{\ominus}$ in which X is aryl, Y is an anion of an inorganic or organic acid, and B is formyl; or A is acetyl and B is dialkoxyphosphinylmethyl of the formula

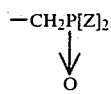

in which Z is lower alkoxy; and $R_8$ is lower alkoxymethyl or lower alkanoyloxymethyl when B is formyl or R is carboxyl, lower alkoxycarbonyl, mono(lower alkyl)carbamoyl or di(lower alkyl)-carbamoyl when B is dialkoxyphosphinylmethyl to give a polyene compound of formula I.

With respect to embodiment II, aryl denoted by X includes all known aryl groups but especially mononuclear aryl groups such as phenyl, lower alkyl-substituted phenyl or lower alkoxy-substituted phenyl (e.g. tolyl, xylyl, mesityl and p-methoxyphenyl). Of the inorganic acid anions denoted by Y, chloride, bromide and hydrosulfate ions are preferred. Of the organic acid anions denoted by Y, the tosyloxy ion is preferred. The lower alkoxy groups denoted by Z preferably have from 1 to 6 carbon atoms (e.g. methoxy or ethoxy).

If desired, the carboxylic acid of formula I obtained by either Embodiment can be converted into a carboxylic acid ester or into an amide. The carboxylic acid ester of formula I then can be converted into a carboxylic acid of formula I. Additionally, the resulting carboxylic acid or carboxylic acid ester of formula I can be converted to a corresponding alcohol which in turn can be esterified or etherified.

In regard to Embodiment I, a ketone of formula III can be converted into a polyene compound of formula IA according to various preferred methods. One method of forming a compound of formula IA wherein $R'_2$ is hydrogen comprises:

(a) reducing a ketone of formula III in a known manner to give a corresponding alcohol of the formula:

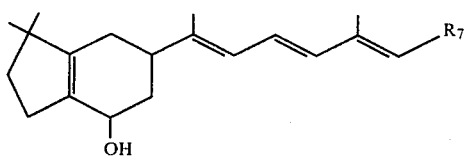

wherein $R_7$ is as above;

(b) dehydrating the alcohol of formula IIIB; and (c) dehydrogenating the dehydration product of step "b" to give a polyene compound of formula IA in which $R'_2$ is hydrogen.

The reduction according to step "a" of a ketone of formula III in which $R_7$ is as above with the exception of a carboxyl group, to give a corresponding alcohol of formula IIIB is conveniently carried out using a complex metal hydride in the presence of a solvent at a low temperature. Preferred complex metal hydrides are those which selectively reduce the oxo group present on the ring of Compound III (e.g. alkali metal borohydrides or alkaline earth metal borohydrides, especially sodium borohydride). Especially suitable solvents are lower alkanols, particularly methanol. The reduction is conveniently carried out at the freezing point of the reaction mixture.

The dehydration of an alcohol of formula IIIB according to step "b" proceeds especially readily when the alcohol is firstly transformed into a corresponding mesylate of formula IIIB by treatment with a methanesulfonic acid halide (e.g. methanesulfonic acid chloride) in the presence of an amine base (e.g. collidine). Methanesulfonic acid is then cleaved from the resulting mesylate by acid treatment in the warm, preferably by the action of a 5% by volume sulfur dioxide solution in dimethylformamide at about 65° C.

The resulting compound of step "b" has the formula:

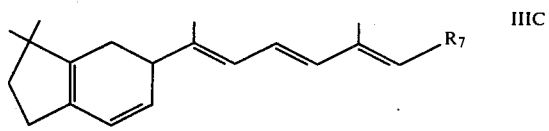

wherein $R_7$ is as above, and is subsequently dehydrogenated according to step "c" to give a polyene compound of formula IA in which $R'_2$ is hydrogen. Dehydrogenation generally occurs by treatment of Compound IIIC with an oxidizing agent in a solvent at room temperature. Preferably, Compound IIIC is treated with 2,3-dichloro-5,6-dicyano-1,4-benzoquinone in dioxan.

In accordance with Embodiment I of the present invention, a method of forming compounds of formula IA wherein $R'_2$ is lower alkoxy comprises:

(a) etherifying an enol of the formula:

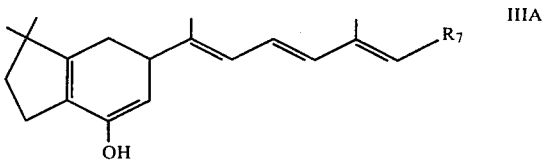

wherein $R_7$ is as above, which is in equilibrium with the corresponding ketone of formula III; and (b) dehydrogenating the resulting ether to give a ketone of formula IA in which $R'_2$ is lower alkoxy.

The aforementioned etherification according to step "a" of an enol of formula IIIA is conveniently carried out by firstly reacting said enol with a lower alkylating agent (e.g. an orthoformic acid lower alkyl ester such as methyl orthoformate) in the presence of a small, catalytical amount of a hydrohalic acid such as hydrochloric acid or a mineral acid such as sulfuric acid. The dehydrogenation according to step "b" of the resulting lower alkyl ether to give a polyene compound of formula IA in which R'2 is lower alkoxy is conveniently carried out using an oxidizing agent (e.g. manganese dioxide or, especially, oxygen or an oxygen-containing gas such as air) at room temperature.

The ketones of formula III which are used as the starting materials in Embodiment I are novel. The ketones can be obtained by (a) reacting a compound of the formula:

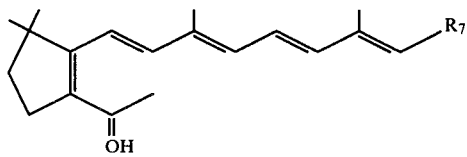

wherein $R_7$ is as above, with a tri(lower alkyl)halosilane (e.g. trimethylchlorosilane) in the presence of a base (preferably an amine base such as triethylamine) to form a silyl ether intermediate of the formula:

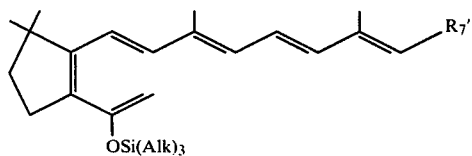

wherein Alk is lower alkyl and $R'_7$ is tri(lower alkyl)-siloxymethyl, lower alkoxymethyl, lower alkanoyloxymethyl, tri(lower alkyl)siloxycarbonyl, lower alkoxycarbonyl, mono(lower alkyl)carbamoyl or di(lower alkyl)carbamoyl; and (b) cyclizing this intermediate to give a ketone of formula III.

Illustratively, the cyclization occurs by heating compound IIA in a solvent (preferably by heating in dimethylformamide to about 150° C.) and cleaving the tri(-lower alkyl)-silanol.

In accordance with Embodiment II, phosphonium salts of formula IV are reacted with aldehydes of formula V according to a Wittig procedure, or ketones of formula IV are reacted with phosphonates of formula V according to a Horner procedure.

The Wittig reaction is carried out in a known manner in the presence of an acid binding agent, (e.g., in the presence of a strong base such as butyl lithium, sodium hydride or the sodium salt of dimethyl sulphoxide). If desired, the reaction can occur in a solvent (e.g. an ether such as diethyl ether or tetrahydrofuran or an aromatic hydrocarbon such as benzene). Although not critical, the reaction generally proceeds at a temperature between room temperature and the boiling point of the reaction mixture.

The Horner reaction is also carried out in a known manner in the presence of a base and, preferably, in the presence of an inert organic solvent. For example, the Horner reaction occurs in the presence of sodium hydride in benzene, toluene, dimethylformamide, tetrahydrofuran, dioxan or 1,2-dimethoxyethane or in the presence of a sodium alcoholate in an alkanol (e.g. sodium methylate in methanol) at a temperature between 0° C. and the boiling point of the reaction mixture.

According to the above Horner procedure, a ketone of formula IV in which $R_1$ and $R_2$ each are hydrogen can be condensed with a phosphonate of formula V in which B is dialkoxyphosphinylmethyl to give a compound of formula I wherein $R_1$ and $R_2$ each are hydrogen.

The aforementioned Wittig and Horner reactions can be carried out in situ, i.e. without isolating the phosphonium salt or phosphonate from the medium in which it is prepared.

The compounds of formula IV, which are used as the starting materials in Embodiment II, are novel.

Illustratively, compounds of formula IV in which A is acetyl, $R_1$ and $R_2$ each are hydrogen (ketones of formula IV) can be prepared by subjecting an indane derivative (which is substituted in the cyclopentene ring corresponding to the desired polyene compound of formula I) or a tetrahydronaphthalene derivative (which is substituted in the cyclohexene ring corresponding to the desired polyene compound of formula I) to acetylation. For example, this acetylation can be carried out in the presence of a Lewis acid.

The preferred Lewis acid acetylating agents are the acetyl halides (e.g. acetyl chloride). Especially suitable Lewis acids are aluminium halides such as aluminium trichloride. The acetylation conveniently is carried out in a solvent (e.g. nitrobenzene) or a chlorinated hydrocarbon (e.g. methylene chloride). The acylation should be carried out at about 0° C. to about +5° C.

Illustratively, the phosphonium salts of formula IV in which A is 1-(triarylphosphonium)-ethyl (which are required for the condensation with an aldehyde of formula V in which B is formyl) can be prepared by reducing a ketone of formula IV in which $R_1$ and $R_2$ each are hydrogen to a corresponding alcohol. The reduction utilizes a complex metal hydride (e.g. sodium borohydride in an alkanol or lithium aluminium hydride in an ether, tetrahydrofuran or dioxan) at about 0° C. to about +5° C. The resulting alcohol is halogenated in the presence of an amine base (e.g. pyridine) using a customary halogenating agent (e.g. phosphorus oxychloride or phosphorus tribromide). The resulting halide is reacted with a triarylphosphine in a solvent (preferably triphenylphosphine in toluene or xylene) to give a desired phosphonium salt of formula IV.

Illustratively, ketones and phosphonium salts of formula IV wherein $R_1$ and $R_2$ are halogen or lower alkoxy can be prepared by converting a corresponding phenol in a known manner into a corresponding lower alkoxy-substituted derivative of formula IV. The conversion occurs by reacting said corresponding phenol with a lower alkylating agent (e.g. a lower alkyl halide or a lower alkanol in the presence of an acid agent).

To obtain the aforementioned phenols, a ketone of formula IV in which $R_1$ and $R_2$ each are hydrogen illustratively is nitrated by treatment with a mixture of concentrated nitric acid and concentrated sulfuric acid. The resulting nitro group which is preferably introduced in the ortho-position to the acetyl group is catalytically reduced in a known manner (e.g. in the presence of Raney-nickel) to an amino group which is then replaced by a hydroxy group via a diazonium salt in a known manner.

If the diazonium salt prepared from an amine is treated in the warm with a copper (I) halide, there is obtained a corresponding halo derivative of the ketone of formula IV. By treating said halo derivative with nitric acid it is possible to introduce a nitro group in the meta-position to the acetyl group. In the manner previously described, the nitro group can be replaced by hydroxy or halogen. By converting the hydroxy group into a lower alkoxy group there can be obtained ketones of formula IV which carry similar or mixed substitution.

A halogen atom present on the aromatic nucleus can be removed, if desired, by reduction in a known manner. The starting materials of formula V, which are utilized in Embodiment II, are known.

In accordance with the process of the present invention, a carboxylic acid of formula I can be converted in a known manner (e.g. by treatment with thionyl chloride, perferably in pyridine or phosphorus trichloride in toluene) into an acid chloride. The resulting acid chloride can be converted by reaction with an alcohol into an ester or by reaction with an amine into a corresponding amide.

A carboxylic acid ester of formula I can be hydrolyzed in a known manner (e.g. by treatment with alkali, especially by treatment with aqueous-alcoholic sodium hydroxide or potassium hydroxide) at a temperature between room temperature and the boiling point of the mixture and then amidated via an acid halide or as described hereinafter.

A carboxylic acid ester of formula I can be converted directly into a corresponding amide. For example, the ester is advantageously treated with lithium amide at room temperature.

A carboxylic acid or a carboxylic acid ester of formula I can be reduced in a known manner to give a corresponding alcohol of formula I. The reduction is advantageously carried out using a metal hydride or alkyl metal hydride in an inert solvent. Especially suitable hydrides are the mixed metal hydrides such as lithium aluminium hydride or bis[methoxy-ethylenoxy]-sodium aluminium hydride. Suitable solvents are, inter alia, ether, tetrahydrofuran or dioxan when lithium aluminium hydride is used and ether, hexane, benzene or toluene when diisobutyl aluminium hydride or bis[methoxy-ethylenoxy]-sodium aluminium hydride is utilized.

An alcohol of formula I can be etherified with an alkyl halide (e.g. ethyl iodide), for example, in the presence of a base (preferably sodium hydride) in an organic solvent (e.g. dioxan, tetrahydrofuran or 1,2-dimethoxyethane and dimethylformamide) or in the presence of an alkali metal alcoholate in an alkanol at a temperature between 0° C. and room temperature.

An alcohol of formula I can also be esterified by treatment with an alkanoyl halide or anhydride, conveniently in the presence of a base (e.g. pyridine or triethylamine) at a temperature between room temperature and the boiling point of the mixture.

A carboxylic acid of formula I forms salts with bases, especially with the alkali metal hydroxides and preferably with sodium hydroxide or potassium hydroxide.

The compounds of formula I can occur as cis/trans mixtures which, if desired, can be separated into cis and trans components or isomerised to the all-trans compounds in a known manner.

The polyene compounds of formula I are useful as medicaments. They can be used for the topical and systemic therapy of benign and malignant neoplasms and of premalignant lesions as well as for the systemic and topical prophylaxis of the said conditions. They are also suitable for the topical systemic therapy of acne, psoriasis and other dermatoses accompanied with an intensified or pathologically altered cornification as well as of inflammatory and allergic dermatological conditions. The polyene compounds of formula I can moreover be used for the control of disorders of the mucous membranes associated with inflammatory or degenerative or metaplastic changes.

The polyene compounds of the present invention are active in extraordinarily small dosages.

With a daily dosage of 1 mg/kg administered to animals there are shown after 14 days (a total of 10 application days) the first symptoms of a A-hypervitaminosis which manifests itself in bone fractures without the appearance of weight decrease, hair loss or scaling of the skin.

The tumor-inhibiting activity of the present polyene compounds is significant. In a papilloma test, tumors induced with dimethylbenzanthracene and croton oil regress. In intraperitoneal administration of all-trans-7-(3,3-dimethyl-7-methoxy-5-indanyl)-3-methyl-octa-2,4,6-trien-1-oic acid ethyl ester, the diameter of the papilloma decreased over 2 weeks by 64% at a dosage of 3 mg/kg/week; by 44% at a dosage of 1.5 mg/kg/week; and by 40% at a dosage of 0.75 mg/kg/week. In oral administration of all-trans-7-(3,3-dimethyl-7-methoxy-5-indanyl)-3-methyl-octa-2,4,6-trien-1-oic acid ethyl ester, the diameter of the induced tumors decreased over 2 weeks (5 individual doses/week) by 41% at a dosage of 10 mg (5×2 mg)/kg/week; and by 24% at a dosage of 2.5 mg (5×0.5 mg)/kg/week.

The polyene compounds of formula I can be used as medicaments. For example, the inventive compounds can be utilized in the form of pharmaceutical preparations which contain the compounds in association with a compatible pharmaceutical carrier. Illustratively, the pharmaceutical preparations suitable for systemic administration can be prepared by adding a polyene compound of formula I as the active ingredient to non-toxic, inert, solid or liquid carriers which are conventionally used in such preparations. The pharmaceutical preparations can be administered enterally or parenterally. For enteral administration, the pharmaceutical preparations suitably take the form of tablets, capsules, dragees, syrups, suspensions, solutions and suppositories. For parenteral administration, the pharmaceutical preparations suitably take the form of infusion or injection solutions.

The dosages in which the present polyene compounds are administered can vary according to the particular pharmaceutical dosage form and mode of administration as well as according to the requirements of the patient.

The polyene compounds of formula I can be administered in amounts of ca 0.01 mg to ca 5 mg daily in one or more dosages. A preferred form of administration comprises capsules containing ca 0.1 mg to ca 1.0 of active ingredient.

The pharmaceutical preparations can contain inert as well as pharmacodynamically active additives. For example, tablets or granulates can contain binding agents, filling agents, carrier materials or diluents. Liquid preparations can take the form of, for example sterile solutions which are miscible with water. In additon to the active ingredient, capsules can contain a filling agent or thickening agent. Furthermore, flavor-improving additives, substances normally used as preservatives, stabilizers, wetting and emulsifying agents as well as salts for varying the osmotic pressure, buffers and other additives may also be present.

The aforementioned carrier substances and diluents can be organic or inorganic in nature; (e.g. water, gelatin, lactose, starch, magnesium stearate, talc, gum arabic, polyalkyleneglycols and the like). All adjuvants used in the preparation of the pharmaceutical preparations must be non-toxic.

For topical administration, the pharmaceutical preparations are conveniently provided in the form of ointments, tinctures, creams, solutions, lotions, sprays, suspensions and the like. Ointments, creams and solutions are preferred. These pharmaceutical preparations for topical administration can be prepared by mixing the present polyene compounds with non-toxic, inert, solid or liquid carriers which are suitable for topical administration and which are customarily utilized in such preparations.

For topical administration, there are suitably used ca 0.01% to ca 0.3%, preferably 0.02% to 0.1% solutions and ca 0.05% to ca 5%, preferably ca 0.05% to ca 1%, ointments or creams.

The pharmaceutical preparations may contain an antioxidant (e.g. tocopherol, N-methyl-$\gamma$-tocopheramine, butylated hydroxy-anisole or butylated hydroxytoluene).

The following Examples illustrate the present invention. Unless otherwise indicated, temperature is in degrees Celsius (°C.) and the ether is diethyl ether.

EXAMPLE 1

A capsule fill mass containing the following ingredients was prepared:

| | |
|---|---|
| all-trans-7-(3,3-Dimethyl-7-methoxy-5-indanyl)-3-methyl-octa-2,4,6-trien-1-oic ethyl ester | 0.1 mg |
| Wax mixture | 50.5 mg |
| Vegetable oil | 98.9 mg |
| Trisodium salt of ethylenediaminetetraacetic acid | 0.5 mg |
| Individual weight of one capsule | 150 mg |
| Active substance content of one capsule | 0.1 mg |

EXAMPLE 2

An ointment of the following composition, containing 0.1% of active ingredient, was prepared:

| | |
|---|---|
| all-trans-7-(3,3-dimethyl-7-methoxy-5-indanyl)-3-methyl-octa-2,4,6-trien-1-oic acid ethyl ester | 0.1 g |
| Cetyl alcohol | 2.7 g |
| Lanolin | 6.0 g |
| Vaseline | 15.0 g |
| Distilled water q.s. ad | 100.0 g |

EXAMPLE 3

21.7 g of [1-(1,1,3,3-tetramethyl-5-indanyl)ethyl]-triphenylphosphonium bromide were suspended in 80 ml of absolute ether and treated dropwise under an inert gas atmosphere with 20 ml of a 2-M n-butyl lithium solution. The internal temperature was held below 30° C. by slight cooling. The dark red solution was stirred at room temperature for 4 hours, cooled to 0° C. and treated dropwise with 6.4 g of 5-formyl-3-methyl-penta-2,4-dienoic acid ethyl ester dissolved in 40 ml of absolute ether. The resulting mixture was stirred at room temperature for 15 hours, introduced into 200 ml of water and extracted with hexane. The hexane extract was extracted three times with methanol/water, dried over sodium sulfate and concentrated under reduced pressure. The residue was purified by adsorption on silica gel using hexane/ether (19:1 parts by volume) for the elution. The all-trans-7-(1,1,3,3-tetramethyl-5-indanyl)-3-methyl-octa-2,4,6-trien-1-oic acid ethyl ester obtained from the eluate melts at 64°-65° C. after recrystallization from hexane/ether.

EXAMPLE 4

87.8 g of acetyl chloride were dissolved in 240 ml of nitrobenzene. 149.2 g of aluminium chloride were introduced portionwise into the resulting solution. The resulting mixture was cooled to 0°-5° C. and then treated dropwise while cooling strongly with a solution of 195.0 g of 1,1,3,3-tetramethyl-indane in 360 ml of nitrobenzene. The temperature should not rise above 5° C. The mixture was stirred at 0° C. for 15 hours, introduced into 3 liters of ice/water and extracted with ether. The ether extract was washed twice with a 2-N sodium hydroxide solution and twice with a saturated sodium chloride solution, dried over sodium sulfate and concentrated, initially in a water-jet vacuum and then in a high vacuum to remove the nitrobenzene. The residual oily 1,1,3,3-tetramethyl-5-indanyl methyl ketone boils at 100°-103° C./0.5 mmHg.

EXAMPLE 5

2.66 g of lithium aluminium hydride were treated with 40 ml of absolute ether. While cooling to 0°-5° C. there were added dropwise within 30 minutes 26 g of 1,1,3,3-tetramethyl-5-indanyl methyl ketone. After a further 30 minutes, the resulting mixture was cautiously treated dropwise with 25 ml of a saturated sodium sulfate solution. The resulting solution was filtered. The filtrate was washed once with a 1-N sodium hydroxide solution and twice with a saturated sodium chloride solution, dried over sodium sulfate and evaporated under reduced pressure to remove the solvent. The residual oily $\alpha$-1,1,3,3-pentamethyl-5-indanemethanol, was uniform according to thin-layer chromatography using hexane/ether (80:20 parts by volume) as an eluent.

EXAMPLE 6

24.0 g of $\alpha$-1,1,3,3-pentamethyl-5-indanemethanol were dissolved in 20 ml of absolute ether and 100 ml of absolute hexane. After the addition of 2 drops of pyridine, the solution was treated dropwise at 0°-5° C. over a period of 30 minutes with 16.2 g of phosphorus tribromide dissolved in 80 ml of absolute hexane. After stirring for a further hour at 0°-5° C., the product is introduced into ice/water and exhaustively extracted with ether. The ether extract is washed twice each time with a saturated sodium bicarbonate solution and sodium chloride solution, dried over sodium sulfate and evaporated under reduced pressure to remove the solvent. The residual oily 5-(1-bromoethyl)-1,1,3,3-tetramethyl-indane is uniform according to thin-layer chromatography with an eluent of hexane/ether (95:5 parts by volume).

EXAMPLE 7

26.3 g of triphenylphosphine were dissolved in 120 ml of xylene. The resulting solution was treated with 30.9 g of 5-(1-bromo-ethyl)-1,1,3,3-tetramethyl-indane dissolved in 60 ml of xylene. The resulting mixture was warmed to 100° C. while stirring and kept at this temperature for 12 hours. The thick-oily 1-(1,1,3,3-tetramethyl-5-indanyl)ethyltriphenylphosphonium bromide which thereby separated and which crystallized after seeding melted at 151°-156° C. after recrystallization from methylene chloride/toluene (crystals contain 0.3 equivalent of toluene).

EXAMPLE 8

2.2 g of 1,1,3,3-tetramethyl-5-indanyl methyl ketone and 2.6 g of 3-methyl-6-(diethoxyphosphinyl)-2,4-hexadienoic acid ethyl ester were dissolved in 7 ml of dimethylformamide. The resulting solution was treated dropwise under argon at room temperature while stirring with a sodium ethanolate solution (prepared from 0.3 g of sodium and 7 ml of ethanol) and subsequently stirred at 70° C. for 18 hours. The resulting mixture was then introduced into ice/water and extracted with ether. The ether extract was washed with a saturated sodium chloride solution, dried over sodium sulfate and evaporated under reduced pressure. The residual all-trans-7-(1,1,3,3-tetramethyl-5-indanyl)-3-methyl-octa-2,4,6-trien-1-oic acid ethyl ester, a dark oil, was purified by adsorption on silica gel using hexane/ether (9:1 parts by volume) for the elution. The ester melted at 64°–65° C. after recrystallization from hexane/ether.

EXAMPLE 9

18.9 g of all-trans-7-(1,1,3,3-tetramethyl-5-indanyl)-3-methyl-octa-2,4,6-trien-1-oic acid ethyl ester were dissolved in 200 ml of ethanol at 50° C. and treated dropwise while stirring with a solution of 12 g of potassium hydroxide in 50 ml of water. The resulting mixture was stirred at 50° C. for 24 hours, cooled, introduced into ice-water, acidified to pH 2 with 3-N sulfuric acid and extracted twice with methylene chloride. The methylene chloride extract was washed with saturated sodium chloride solution, dried over anhydrous sodium sulfate and concentrated under reduced pressure. The residual all-trans-7-(1,1,3,3-tetramethyl-5-indanyl)-3-methyl-octa-2,4,6-trien-1-oic acid melted at 216°–217° C. after recrystallization from methylene chloride/hexane.

EXAMPLE 10

0.4 g of phosphorus trichloride were introduced under argon into a suspension of 2 g of all-trans-7-(1,1,3,3-tetramethyl-5-indanyl)-3-methyl-octa-2,4,6-trien-1-oic acid in 25 ml of toluene. The resulting mixture was stirred at room temperature and a clear solution gradually formed. After 18 hours, the clear solution decanted off from the phosphorus acid formed. The clear yellow solution of the resulting acid chloride was introduced dropwise under argon at a temperature between 0° C. and 10° C. into a solution of 3 ml of ethylamine in 40 ml of methylene chloride. The mixture was stirred at room temperature for one further hour, introduced into a saturated sodium chloride solution and extracted twice with methylene chloride. The methylene chloride extract was washed with a saturated sodium chloride solution, dried over anhydrous sodium sulfate and evaporated under reduced pressure. The residual all-trans-7-(1,1,3,3-tetramethyl-5-indanyl)-3-methyl-octa-2,4,6-triene-1-monoethylamide melted at 164°–165° C. after recrystallization from methylene chloride/hexane.

EXAMPLE 11

In a manner analogous to that described in Example 3 from [1-(6-methoxy-1,1,3,3-tetramethyl-5-indanyl)ethyl]-triphenylphosphonium bromide and 5-formyl-3-methyl-penta-2,4-dienoic acid ethyl ester there can be obtained all-trans-7-(6-methoxy-1,1,3,3-tetramethyl-5-indanyl)-3-methyl-octa-2,4,6-trien-1-oic acid ethyl ester of melting point 109°–110° C.

EXAMPLE 12

[1-(6-methoxy-1,1,3,3-tetramethyl-5-indanyl)ethyl]-triphenylphosphonium bromide can be prepared in a manner analogous to that described in Examples 4–7 from 1,1,3,3-tetramethyl-5-methoxy-indane via (7-methoxy-1,1,3,3-tetramethyl-5-indanyl) methyl ketone, 7-methoxy-α-1,1,3,3-pentamethyl-5-indanemethanol and 5-(1-bromoethyl)-7-methoxy-1,1,3,3-tetramethylindane.

EXAMPLE 13

56.3 g of 1,1,3,3-tetramethyl-5-indanol were dissolved in 600 ml of methyl ethyl ketone. The resulting solution was treated with 80 g of solid potassium carbonate and 200 ml of methyl iodide were added thereto. The resulting mixture was then warmed to 40° C. and stirred for 24 hours. For working-up, the mixture was introduced into ice/water and extracted with ether. The ether extract was washed three times with a 5-N sodium hydroxide solution and three times with a saturated sodium chloride solution, dried over sodium sulfate and evaporated under reduced pressure. The residual yellowish oil, 1,1,3,3-tetramethyl-5-methoxy-indane, was uniform according to thin-layer chromatography with hexane as the eluent.

EXAMPLE 14

5.0 g of all-trans-7-(4,5,6,7-tetrahydro-3,3-dimethyl-7-oxo-5-indanyl)-3-methyl-octa-2,4,6-trien-1-oic acid ethyl ester dissolved in 50 ml of methanol were treated portionwise at 0°–5° C. with 1.1 g of sodium borohydride. After completion of the addition, the resulting mixture was stirred at room temperature for a further hour and subsequently introduced into ice/water. The solution, made weakly acid with dilute hydrochloric acid, was extracted several times with methylene chloride. After washing with a saturated sodium chloride solution, the combined methylene chloride phases were dried over sodium sulfate and evaporated to remove the solvent. The residual oily yellow all-trans-7-(4,5,6,7-tetrahydro-3,3-dimethyl-7-hydroxy-5-indanyl)-3-methyl-octa-2,4,6-trien-1-oic acid ethyl ester was uniform according to thin-layer chromatography using hexane/ether (4:1 parts by volume) as the eluent.

EXAMPLE 15

4.7 g of all-trans-7-(4,5,6,7-tetrahydro-3,3-dimethyl-7-hydroxy-5-indanyl)-3-methyl-octa-2,4,6-trien-1-oic acid ethyl ester were dissolved in 34 ml of dimethylformamide. The solution was treated with 4.8 g of methanesulfonic acid chloride and then with 12 ml of symcollidine. The solution, which warmed to 30° C., was cooled to 10° C. and treated with 2 ml of a 5% by volume sulfur dioxide solution of diemthylformamide. After warming to 65° C. for 3 hours, the mixture was introduced into ice/water and, after acidification with dilute hydrochloric acid, extracted twice with ether. The ether phases were washed with a soda solution and a saturated sodium chloride solution and dried over sodium sulfate. The dark oil remaining after removal of the solvent was purified by adsorption on silica gel using hexane/ether (20:1 parts by volume) for the elution. The resulting all-trans-7-(4,5-dihydro-3,3-dimethyl-5-indanyl)-3-methyl-octa-2,4,6-trien-1-oic acid ethyl ester was a yellowish oil.

EXAMPLE 16

2.7 g of all-trans-7-(4,5-dihydro-3,3-dimethyl-5-indanyl)-3-methyl-octa-2,4,6-trien-1-oic acid ethyl ester were dissolved in 35 ml of dioxan. The resulting solution was treated with 1.8 g of 2,3-dichloro-5,6-dicyano-1,4-benzoquinone with the exclusion of light. The resulting mixture was stirred at room temperature for 12 hours and subsequently filtered. The filtrate was taken up in ether, washed once with a sodium bisulfite solution and twice with a saturated sodium chloride solution, dried over sodium sulfate and evaporated under reduced pressure. The dark residue was purified by adsorption on silica gel using hexane/ether (19:1 parts by volume) for the elution. The resulting all-trans-7-(3,3-dimethyl-5-indanyl)-3-methyl-octa-2,4,6-trien-1-oic acid ethyl ester was a yellow oil of boiling point (bulb-tube) 230° C./0.08 mmHg.

EXAMPLE 17

After the addition of 500 ml of dimethylformamide, 154 g of all-trans-9-(2-acetyl-5,5-dimethyl-1-cyclopenten-1-yl)-3,7-dimethyl-nona-2,4,6,8-tetraen-1-oic acid ethyl ester were introduced under nitrogen into a mixture of 111 g of triethylamine and 60 g of trimethylchlorosilane. The resulting mixture was heated to 150° C. and a clear solution formed. A sample of the clear solution removed after 5 hours contained according to thin-layer chromatography, practically no more educt. The cooled solution was poured with ether and water into ice/water. After washing with dilute hydrochloric acid, saturated bicarbonate solution and saturated sodium chloride solution, the ether extract was dried over sodium sulfate and evaporated to remove the solvent. The residual oily all-trans-7-(4,5,6-tetrahydro-3,3-dimethyl-7-oxo-5-indanyl)-3-methyl-octa-2,4,6-trien-1-oic acid ethyl ester melted at 86°–88° C. after crystallization from ether/hexane.

EXAMPLE 18

7.0 g of all-trans-7-(4,5,6,7-tetrahydro-3,3-dimethyl-7-oxo-5-indanyl)-3-methyl-octa-2,4,6-trien-1-oic acid ethyl ester (prepared as described in Example 17 were dissolved in 50 ml of methyl orthoformate. The resulting solution was treated with 30 drops of concentrated sulfuric acid and stirred at room temperature for 36 hours with access of air. The dark mixture was introduced into ice/sodium bicarbonate solution and extracted twice with ether. The ether extracts were washed with a saturated sodium chloride solution, dried over sodium sulfate and concentrated under reduced pressure. The residual oily yellowish all-trans-7-(3,3-dimethyl-7-methoxy-5-indanyl)-3-methyl-octa-2,4,6-trien-1-oic acid ethyl ester was purified by adsorption on silica gel using ether/hexane (1:19 parts by volume) for the elution, UV: 348 nm ($\epsilon$—33,000).

EXAMPLE 19

In a manner analogous to that described in Example 3, from [1-(5,6,7,8-tetrahydro-5,5,8,8-tetramethyl-2-naphthyl)-ethyl]-triphenylphosphonium bromide and 5-formyl-3-methyl-penta-2,4-dienoic acid ethyl ester there can be obtained all-trans-7-(5,6,7,8-tetrahydro-5,5,8,8-tetramethyl-2-naphthyl)-3-methyl-octa-2,4,6-trien-1-oic acid ethyl ester of melting point 103°–104° C.

EXAMPLE 20

[1-(5,6,7,8-tetrahydro-5,5,8,8-tetramethyl-2-naphthyl)ethyl]-triphenylphosphonium bromide can be prepared in a manner analogous to that described in Examples 4–7 from 5,6,7,8-tetrahydro-5,5,8,8-tetramethyl-naphthalene via (5,6,7,8-tetrahydro-5,5,8,8-tetramethyl-2-naphthyl) methyl ketone, 5,6,7,8-tetrahydro-α-5,5,8,8-pentamethyl-2-naphthalenemethanol and 2-(bromoethyl)-5,6,7,8-tetrahydro-5,5,8,8-tetramethyl-naphthalene.

EXAMPLE 21

In a manner analogous to that described in Example 3 from [1-(3-methoxy-5,6,7,8-tetrahydro-5,5,8,8-tetramethyl-2-naphthyl)ethyl]-triphenylphosphonium bromide and 5-formyl-3-methyl-penta-2,4-dienoic acid ethyl ester there can be obtained all-trans-7-(3-methoxy-5,6,7,8-tetrahydro-5,5,8,8-tetramethyl-2-naphthyl)-3-methyl-octa-2,4,6-trien-1-oic acid ethyl ester of melting point 103°–104° C.

EXAMPLE 22

[1-(3-methoxy-5,6,7,8-tetrahydro-5,5,8,8-tetramethyl-2-naphthyl)ethyl]-triphenylphosphinium bromide can be prepared in a manner analogous to that described in Examples 4–7 from 3-methoxy-5,6,7,8-tetrahydro-5,5,8,8-tetramethyl-2-naphthyl) methyl ketone, 3-methoxy-5,6,7,8-tetrahydro-5,5,8,8-tetramethyl-2-naphthalenemethanol and 2-(1-bromoethyl)-3-methoxy-5,6,7,8-tetrahydro-5,5,8,8-tetramethyl-naphthalene.

I claim:

1. A polyene compound of the formula:

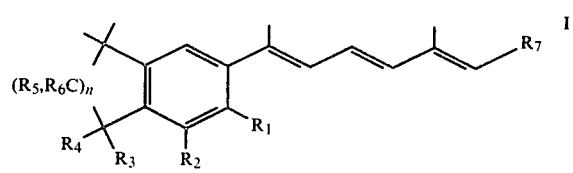

wherein $R_1$ and $R_2$ each are hydrogen, halogen or lower alkoxy; $R_3$, $R_4$, $R_5$ and $R_6$ each are hydrogen or lower alkyl; $R_7$ is hydroxymethyl, lower alkoxymethyl, lower alkanoyloxymethyl, carboxyl, lower alkoxycarbonyl, mono(lower alkyl)carbamoyl or di(lower alkyl)carbamoyl; and n is 1 or 2 or the alkali metal salts thereof.

2. The polyene compound of claim 1 wherein $R_3$, $R_4$, $R_5$ and $R_6$ each are hydrogen.

3. The polyene compound of claim 1 wherein $R_1$ and $R_2$ each are hydrogen or lower alkoxy.

4. The polyene compound of claims 1, 2 or 3 wherein $R_7$ is lower alkoxycarbonyl, mono(lower alkyl)carbamoyl or di(lower alkyl)carbamoyl.

5. The compound of claim 1 wherein the compound is all-trans-7-(1,1,3,3-tetramethyl-5-indanyl)-3-methyl-octa-2,4,6-trien-1-oic acid ethyl ester.

6. The compound of claim 1 wherein the compound is all-trans-7-(1,1,3,3-tetramethyl-5-indanyl)-3-methyl-octa-2,4,6-trien-1-oic acid.

7. The compound of claim 1 wherein the compound is all-trans-7-(1,1,3,3-tetramethyl-5-indanyl)-3-methyl-octa-2,4,6-trien-1-oic acid ethylamide.

8. The compound of claim 1 wherein the compound is all-trans-7-(6-methoxy-1,1,3,3-tetramethyl-5-indanyl)-3-methyl-octa-2,4,6-trien-1-oic acid ethyl ester.

9. The compound of claim 1 wherein the compound is all-trans-7-(3,3-dimethyl-5-indanyl)-3-methyl-octa-2,4,6-trien-1-oic acid ethyl ester.

10. The compound of claim 1 wherein the compound is all trans-7-(7-methoxy-3,3-dimethyl-5-indanyl)-3-methyl-octa-2,4,6-trien-1-oic acid ethyl ester.

11. The compound of claim 1 wherein the compound is all-trans-7-(5,6,7,8-tetrahydro-5,5,8,8-tetramethyl-2-naphthyl)-3-methyl-octa-2,4,6-trien-1-oic acid ethyl ester.

12. The compound of claim 1 wherein the compound is all-trans-7-(3-methoxy-5,6,7,8-tetrahydro-5,5,8,8-tetramethyl-2-naphthyl)-3-methyl-octa-2,4,6-trien-1-oic acid ethyl ester.

13. A pharmaceutical preparation containing a polyene compound of the formula:

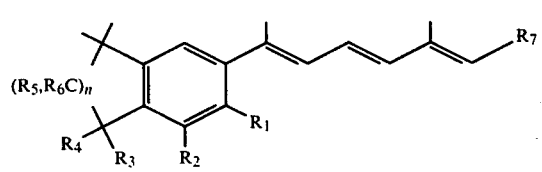

wherein $R_1$ and $R_2$ each are hydrogen, halogen atom or lower alkoxy; $R_3$, $R_4$, $R_5$ and $R_6$ each are hydrogen or lower alkyl; $R_7$ is hydroxymethyl, lower alkoxymethyl, lower alkanoyloxymethyl, carboxyl, lower alkoxycarbonyl, mono(lower alkyl)carbamoyl or di(lower alkyl)carbamoyl group; and n is 1 or 2; in association with a compatible pharmaceutical carrier.

14. The pharmaceutical preparation of claim 13 wherein said polyene compound is all-trans-7-(1,1,3,3-tetramethyl-5-indanyl)-3-methyl-octa-2,4,6-trien-1-oic acid ethyl ester.

15. The pharmaceutical preparation of claim 13 wherein said polyene compound is all-trans-7-(1,1,3,3-tetramethyl-5-indanyl)-3-methyl-octa-2,4,6-trien-1-oic acid.

16. The pharmaceutical preparation of claim 13 wherein said polyene compound is all-trans-7-(1,1,3,3-tetramethyl-5-indanyl)-3-methyl-octa-2,4,6-trien-1-oic acid ethylamide.

17. The pharmaceutical preparation of claim 13 wherein said polyene compound is all-trans-7-(6-methoxy-1,1,3,3-tetramethyl-5-indanyl)-3-methyl-octa-2,4,6-trien-1-oic acid ethyl ester.

18. The pharmaceutical preparation of claim 13 wherein said polyene compound is all-trans-7-(3,3-dimethyl-5-indanyl)-3-methyl-octa-2,4,6-trien-1-oic acid ethyl ester.

19. The pharmaceutical preparation of claim 13 wherein said polyene compound is all-trans-7-(7-methoxy-3,3-dimethyl-5-indanyl)-3-methyl-octa-2,4,6-trien-1-oic acid ethyl ester.

20. The pharmaceutical preparation of claim 13 wherein said polyene compound is all-trans-7-(5,6,7,8-tetrahydro-5,5,8,8-tetramethyl-2-naphthyl)-3-methyl-octa-2,4,6-trien-1-oic acid ethyl ester.

21. The pharmaceutical preparation of claim 13 wherein said polyene compound is all-trans-7-(3-methoxy-5,6,7,8-tetrahydro-5,5,8,8-tetramethyl-2-naphthyl)-3-methyl-octa-2,4,6-trien-1-oic acid ethyl ester.

* * * * *